US012569631B2

(12) United States Patent
Breiwa, III

(10) Patent No.: US 12,569,631 B2
(45) Date of Patent: Mar. 10, 2026

(54) EXOTHERMAL VAPORIZER

(71) Applicant: Dynavap, LLC, DeForest, WI (US)

(72) Inventor: George R. Breiwa, III, Dane, WI (US)

(73) Assignee: DynaVap, LLC, DeForest, WI (US)

( * ) Notice: Subject to any disclaimer, the term of this patent is extended or adjusted under 35 U.S.C. 154(b) by 75 days.

(21) Appl. No.: 16/916,864

(22) Filed: Jun. 30, 2020

(65) Prior Publication Data

US 2021/0007394 A1      Jan. 14, 2021

Related U.S. Application Data

(62) Division of application No. 16/243,879, filed on Jan. 9, 2019, now abandoned, which is a division of
(Continued)

(51) Int. Cl.
| | |
|---|---|
| *A24F 42/60* | (2020.01) |
| *A24F 1/02* | (2006.01) |
| *A24F 7/00* | (2006.01) |
| *A24F 40/10* | (2020.01) |
| *A24F 40/40* | (2020.01) |
(Continued)

(52) U.S. Cl.
CPC ............... *A61M 15/06* (2013.01); *A24F 1/02* (2013.01); *A24F 7/00* (2013.01); *A24F 40/10* (2020.01); *A24F 40/40* (2020.01); *A24F 42/10* (2020.01); *A24F 42/60* (2020.01); *A61M 15/0025* (2014.02); *F28F 1/10* (2013.01); *A24F 2700/03* (2013.01); *A61M 11/048* (2014.02); *A61M 2205/0227* (2013.01);
(Continued)

(58) Field of Classification Search
CPC .......... A24F 40/10; A24F 40/40; A24F 42/60; A61M 15/06; A61M 2205/0227; A61M 2205/3368
See application file for complete search history.

(56) References Cited

U.S. PATENT DOCUMENTS

| | | |
|---|---|---|
| 198,341 A | 12/1877 | Brisbane |
| 253,512 A | 2/1882 | Cole |
(Continued)

FOREIGN PATENT DOCUMENTS

| | | |
|---|---|---|
| CN | 101500443 | 8/2009 |
| CN | 204132401 U | 2/2015 |
(Continued)

OTHER PUBLICATIONS

International Preliminary Report on Patentability dated Jul. 9, 2015, for International Appln. No. PCT/US2013/078067 filed Dec. 27, 2013.
(Continued)

*Primary Examiner* — Russell E Sparks
(74) *Attorney, Agent, or Firm* — Boardman & Clark LLP

(57) ABSTRACT

An exothermal vaporizer is provided. The exothermal vaporizer has a body including an air and vapor mix port, a fluid inlet port in communication with a reservoir, an air inlet, and a wicking material. A mouthpiece is coupled to the body and a temperature indicating cap is removable from the body. A counter flow design exothermal vaporizer, a modular exothermal vaporizer, and a vaporizer which is adjustable to modulate and/or regulate the flow ratio of dilution air and produced vapor are also disclosed.

21 Claims, 22 Drawing Sheets

Related U.S. Application Data application No. 15/210,749, filed on Jul. 14, 2016, now Pat. No. 10,206,425.

(60) Provisional application No. 62/192,432, filed on Jul. 14, 2015, provisional application No. 62/269,834, filed on Dec. 18, 2015.

(51) Int. Cl.

| | |
|---|---|
| *A24F 42/10* | (2020.01) |
| *A61M 15/00* | (2006.01) |
| *A61M 15/06* | (2006.01) |
| *F28F 1/10* | (2006.01) |
| *A61M 11/04* | (2006.01) |

(52) U.S. Cl.
CPC .. *A61M 2205/3368* (2013.01); *F28F 2215/00* (2013.01); *F28F 2220/00* (2013.01)

(56) References Cited

U.S. PATENT DOCUMENTS

| 1,401,876 | A | | 12/1921 | Celeda |
| 2,040,190 | A | | 5/1936 | Torrese |
| 2,132,289 | A | | 10/1938 | De Vita |
| 2,216,303 | A | | 10/1940 | Taylor |
| 2,606,561 | A | | 8/1952 | Doerr |
| 2,721,551 | A | * | 10/1955 | Lobl ....................... A24F 42/60 |
| | | | | 128/202.21 |
| 3,084,698 | A | | 4/1963 | Smith |
| 3,170,468 | A | | 2/1965 | Smith |
| 3,406,693 | A | | 10/1968 | Benoit |
| 3,685,523 | A | | 8/1972 | Labbe |
| 3,780,745 | A | * | 12/1973 | Smith ....................... A24F 1/00 |
| | | | | 131/212.2 |
| 3,863,647 | A | | 2/1975 | Unger |
| 4,145,961 | A | | 3/1979 | Lolli |
| 4,224,953 | A | | 9/1980 | Alvarez |
| 4,774,971 | A | | 10/1988 | Vieten et al. |
| 4,856,542 | A | | 8/1989 | Hollenberg |
| 5,417,227 | A | | 5/1995 | West |
| 5,591,368 | A | | 1/1997 | Fleischhauer |
| 5,687,746 | A | | 11/1997 | Rose |
| 5,743,251 | A | | 4/1998 | Howell |
| 5,878,752 | A | | 3/1999 | Adams |
| 6,095,153 | A | | 8/2000 | Kessler et al. |
| 6,148,826 | A | | 11/2000 | Lancaster |
| 6,164,287 | A | | 12/2000 | White et al. |
| 6,216,705 | B1 | | 4/2001 | Ossepian |
| 7,173,222 | B2 | | 2/2007 | Cox et al. |
| 7,370,435 | B2 | | 5/2008 | Boki et al. |
| 7,415,982 | B1 | | 8/2008 | Sheridan |
| 7,434,584 | B2 | | 10/2008 | Steinberg et al. |
| 7,997,280 | B2 | * | 8/2011 | Rosenthal ............. A61M 15/06 |
| | | | | 131/194 |
| 8,430,106 | B2 | | 4/2013 | Potter et al. |
| 8,869,792 | B1 | | 10/2014 | Lee |
| 9,282,772 | B2 | | 3/2016 | Tucker |
| 9,848,638 | B2 | * | 12/2017 | Morgan .................... A24F 1/32 |
| 10,039,323 | B2 | * | 8/2018 | Schuler .................. A24F 40/42 |
| 10,206,425 | B2 | | 2/2019 | Breiwa, III |
| 2003/0033055 | A1 | | 2/2003 | McRae |
| 2004/0031495 | A1 | | 2/2004 | Steinberg |
| 2006/0196518 | A1 | | 9/2006 | Hon |
| 2007/0074734 | A1 | | 4/2007 | Braunshteyn et al. |
| 2008/0023003 | A1 | | 1/2008 | Rosenthal |

| 2008/0053465 | A1 | | 3/2008 | Tarora |
| 2008/0057218 | A1 | | 3/2008 | Gregg |
| 2008/0149118 | A1 | | 6/2008 | Oglesby et al. |
| 2008/0302374 | A1 | * | 12/2008 | Wengert .................. A24F 42/60 |
| | | | | 131/194 |
| 2009/0032034 | A1 | | 2/2009 | Steinberg et al. |
| 2010/0059070 | A1 | | 3/2010 | Potter et al. |
| 2010/0078035 | A1 | | 4/2010 | Erickson |
| 2011/0036346 | A1 | | 2/2011 | Cohen |
| 2011/0094523 | A1 | | 4/2011 | Thorens et al. |
| 2011/0226236 | A1 | | 9/2011 | Buchberger |
| 2012/0186592 | A1 | | 7/2012 | Schleider |
| 2013/0037041 | A1 | | 2/2013 | Worm |
| 2013/0042865 | A1 | | 2/2013 | Monsees |
| 2013/0192623 | A1 | | 8/2013 | Tucker et al. |
| 2013/0228191 | A1 | | 9/2013 | Newton |
| 2013/0333709 | A1 | | 12/2013 | Shimizu |
| 2014/0186015 | A1 | | 7/2014 | Breiwa, III et al. |
| 2014/0283860 | A1 | | 9/2014 | Stolz |
| 2015/0027458 | A1 | | 1/2015 | Grant |
| 2015/0090279 | A1 | | 4/2015 | Chen |
| 2015/0144146 | A1 | | 5/2015 | Selby |
| 2015/0157053 | A1 | | 6/2015 | Mayor |
| 2015/0173417 | A1 | | 6/2015 | Gennrich |
| 2015/0181937 | A1 | | 7/2015 | Dubief |
| 2015/0245421 | A1 | | 8/2015 | Heczko |
| 2015/0257446 | A1 | | 9/2015 | Chung |
| 2015/0320116 | A1 | | 11/2015 | Bleloch et al. |
| 2015/0342255 | A1 | | 12/2015 | Wu |
| 2016/0021929 | A1 | | 1/2016 | Sawalha |
| 2016/0021933 | A1 | | 1/2016 | Thorens |
| 2016/0198769 | A1 | | 7/2016 | Liu |
| 2016/0235123 | A1 | | 8/2016 | Krietzman |
| 2016/0295915 | A1 | | 10/2016 | Jochnowitz |
| 2016/0309789 | A1 | | 10/2016 | Thomas |
| 2017/0127481 | A1 | | 5/2017 | Gough et al. |
| 2017/0150755 | A1 | | 6/2017 | Batista |

FOREIGN PATENT DOCUMENTS

| DE | 202014000343 | U1 | 2/2014 |
| DE | 202014008768 | U1 | 11/2014 |
| EP | 1867357 | A1 | 12/2007 |
| GB | 1101533 | A | 1/1968 |
| GB | 2473264 | A | 3/2011 |
| JP | 8-508646 | | 9/1996 |
| JP | 2010520742 | | 6/2010 |
| KR | 1012500130000 | | 3/2013 |
| WO | 2007143993 | A2 | 12/2007 |
| WO | 2008015441 | A1 | 2/2008 |

OTHER PUBLICATIONS

International Search Report and Written Opinion dated May 20, 2014, for International Appln. No. PCT/US2013/078067 filed Dec. 27, 2013.

International Search Report and Written Opinion dated Oct. 13, 2016, for International Appln. No. PCT/US2016/042351 filed Jul. 14, 2016.

International Preliminary Report on Patentability dated Jan. 16, 2018, for International Appln. No. PCT/US2016/042351 filed Jul. 14, 2016.

International Search Report and Written Opinion dated Feb. 15, 2019, for International Appln. No. PCT/US2018/063421 filed Nov. 30, 2018.

\* cited by examiner

156

156

154

A

A

156

160

156

158

SECTION A-A

154

125

EXOTHERMAL VAPORIZER

CROSS-REFERENCE TO RELATED APPLICATIONS

This application claims priority to and is a divisional of U.S. Nonprovisional application Ser. No. 16/243,879, filed Jan. 9, 2019, entitled "Diffuser Disc and Diffuser Assembly," which is a divisional of United States Nonprovisional Application Ser. No. 15/210,749 filed Jul. 14, 2016, entitled "Exothermal Vaporizer," now U.S. Pat. No. 10,206,425, which claims priority to United States Provisional Application, Serial No. 62/192,432 filed Jul. 14, 2015, entitled "Exothermal Fluid Vaporizer and Counter Flow Design Exothermal Vaporizer," and claims priority to U.S. Provisional Application, Ser. No. 62/269,834 filed Dec. 18, 2015, entitled "Exothermal Modular Vaporizer," the contents of each of which are hereby incorporated by reference in their entirety herein.

FIELD

The present invention(s) relate to the field of vaporizers, and more specifically to a vaporizer having modular components and a counter flow design for use with an external heating source.

BACKGROUND

"Vaping" or the inhalation of vaporized substances using a vaporizer, electronic cigarette, or similar device, has become increasingly popular since its introduction to the market a short time ago. However, known vaporization devices have certain drawbacks, including power source issues, cumbersome form factors, and difficulty functioning in harsh environmental conditions.

Current devices such as vaporizers and electronic cigarettes function via an electrically heated and controlled vaporization element. This allows for a very precise level of control, but forces complete reliance upon electricity, batteries, charging devices, and connectors. Although battery technology continues to improve and evolve, volumetrically batteries can only store a small fraction of the energy stored in most fuels.

Without the ability to function independent of electricity, the user of current technology devices must carry sufficient stored energy, typically in the form of batteries as well as chargers to convert line voltage or power, such as from a car, to a suitable voltage and current to recharge the batteries contained in the device. The result is a cumbersome experience—not only are the devices themselves large and difficult to handle, but they also often require additional proprietary accessories to maintain functionality.

Another noteworthy drawback of the current generation of existing devices is their susceptibility to failure in harsh environmental conditions. For example, the two conditions often most detrimental to proper functioning are wet and very cold conditions. Water can, in many cases, cause permanent damage to the sensitive electrical componentry of electronic devices. Cold can dramatically affect the ability of the battery systems to provide the necessary power for proper vaporization, sometimes rendering the device completely unusable.

In addition, these known devices cannot also be used for smoking (consumption of dried substances via combustion instead of vaporization). Furthermore, known vaporizer devices likewise may be difficult to clean and/or customize.

Accordingly, there are currently no known devices designed for, or which provide for accurate and repeatable vaporization of fluids or other material, such as smoking material, without the use of an integrated heat source and associated control mechanism. What is needed is a device that allows for easy and consistent vaporization of substances for inhalation that has a smaller form-factor, is easy to clean, and addresses the limitations and other issues faced by current vaporization devices without the need for complex controls, circuitry and/or integrated energy storage components.

SUMMARY

Accordingly, one or more examples of exothermal vaporizers are disclosed.

In particular, an exothermal vaporizer is provided. The exothermal vaporizer has a body including an air and vapor mix port, a fluid inlet port in communication with a reservoir, an air inlet, and a wicking material or evaporation matrix. A mouthpiece is coupled to the body and a temperature indicating cap which is removable from the body.

An exothermal vaporizer having a counter flow design is also disclosed. The exothermal vaporizer includes a body comprising an outer tube. An internal tube or condenser is also provided having a smaller cross-sectional area than the body and retained in position in the body by a mouthpiece or O-rings coupled to the body, wherein the condenser runs or extends the approximate length of the body. An extraction chamber is provided in the tip which is incorporated with the body. A temperature indicating cap is provided and is removable from the body.

An exothermal vaporizer is also provided including a condenser tube which threads into a mouthpiece and is user adjustable to modulate and/or regulate the flow ratio of dilution air and produced vapor. The vaporizer also has a body containing the condenser tube, wherein the mouthpiece and a tip incorporating the extraction chamber are integrated with the body by friction fit O-rings and wherein the condenser tube remains rotationally fixed relative to the body as the mouthpiece is twisted and the tip and condenser tube have one or more interfacing surfaces.

These and other features and advantages of devices, systems, and methods according to this invention are described in, or are apparent from, the following detailed descriptions of various examples of embodiments.

BRIEF DESCRIPTION OF DRAWINGS

Various examples of embodiments of the systems, devices, and methods according to this invention will be described in detail, with reference to the following figures, wherein:

FIG. 9b is a side elevation cross-sectional view of the modular exothermal vaporizer of FIG. 9a, taken from line 9b-9b of FIG. 9a.

FIG. 10 is a perspective view of the modular exothermal vaporizer shown in FIG. 9a.

It should be understood that the drawings are not necessarily to scale. In certain instances, details that are not necessary to the understanding of the invention or render other details difficult to perceive may have been omitted. It should be understood, of course, that the invention is not necessarily limited to the particular embodiments illustrated herein.

DETAILED DESCRIPTION

The present invention relates generally to a vaporizer, and more specifically to a modular vaporizer, which is heated to the vaporizing temperature of the fluid or the active compounds desirable for extraction from the smoking material contained within via any external heat source of sufficient temperature. Among other features, this new category of vaporizer differentiates from other types of vaporizers by completely separating the heat source and its associated control from the vaporizing components and materials.

Figure 1:
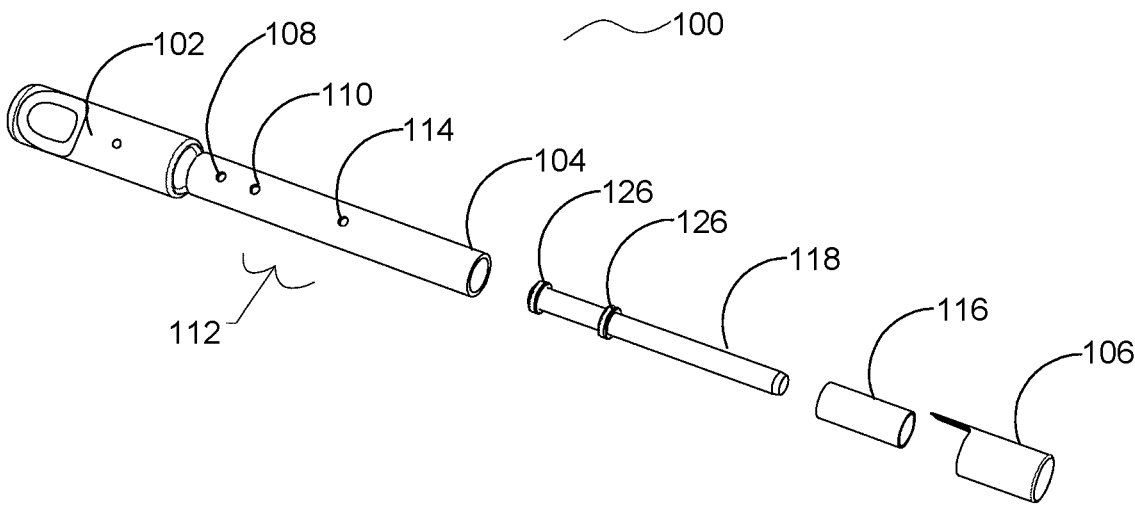
FIG. 1 is an exploded perspective view of an exothermal vaporizer, in various embodiments, as disclosed herein.
Figure 2:
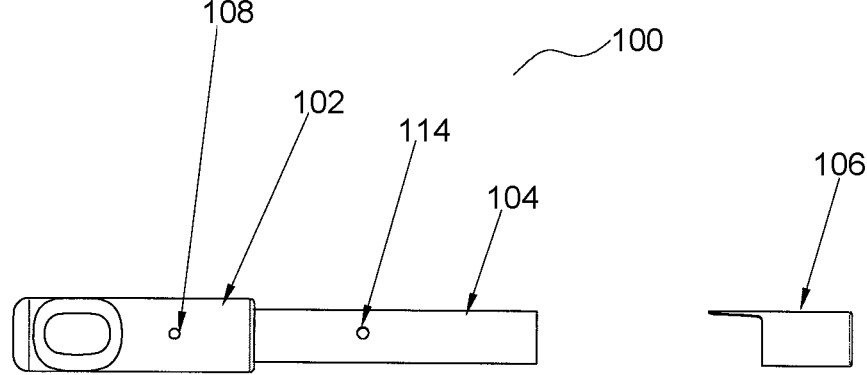
FIG. 2 is a partially exploded elevation view of the exothermal vaporizer of FIG. 1, in various embodiments, as disclosed herein.
Figure 3:
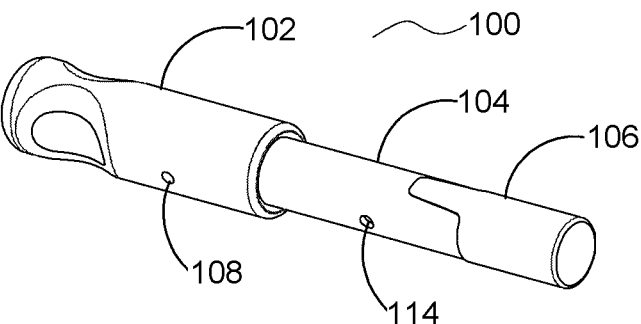
FIG. 3 is a perspective view of the assembled exothermal vaporizer of FIG. 1, in various embodiments, as disclosed herein.
Figure 4:
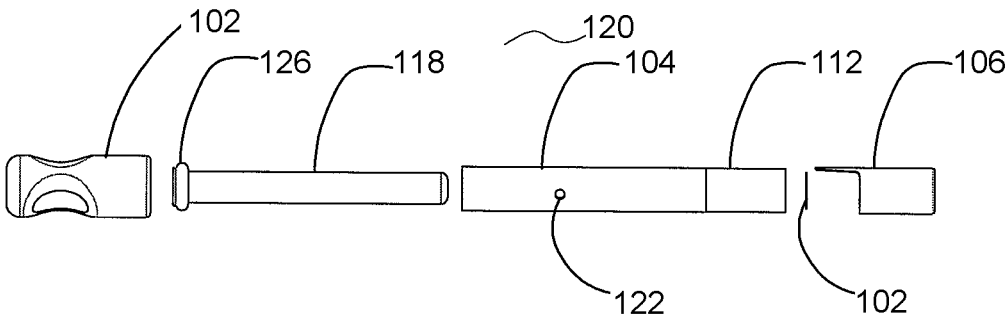
FIG. 4 is an exploded side elevation view of a counter flow design exothermal vaporizer, in various embodiments, as disclosed herein.
Figure 5:
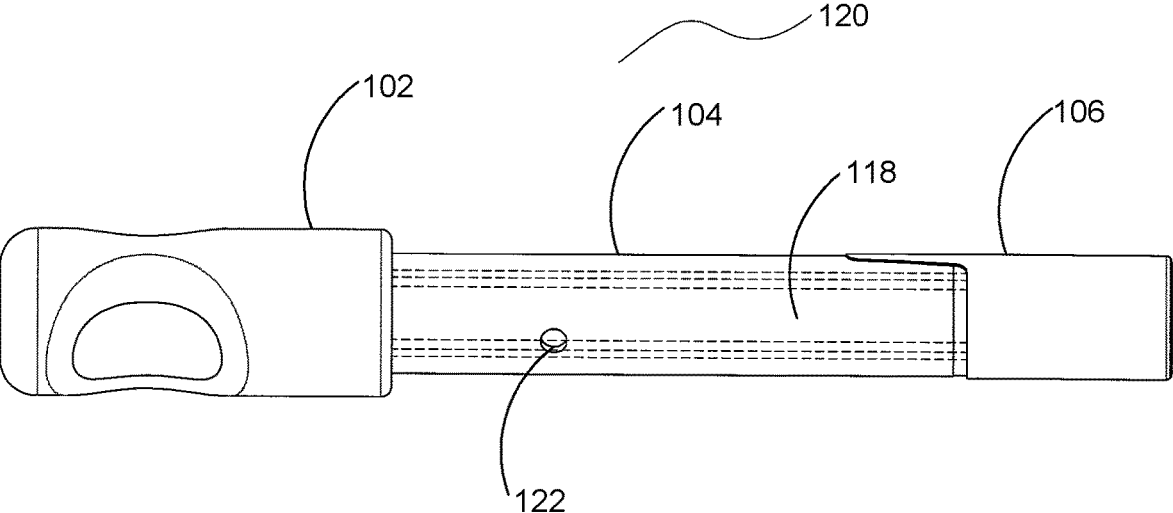
FIG. 5 is a perspective view of an exothermal vaporizer of FIG. 4, in various embodiments, as disclosed herein.
Figure 6:
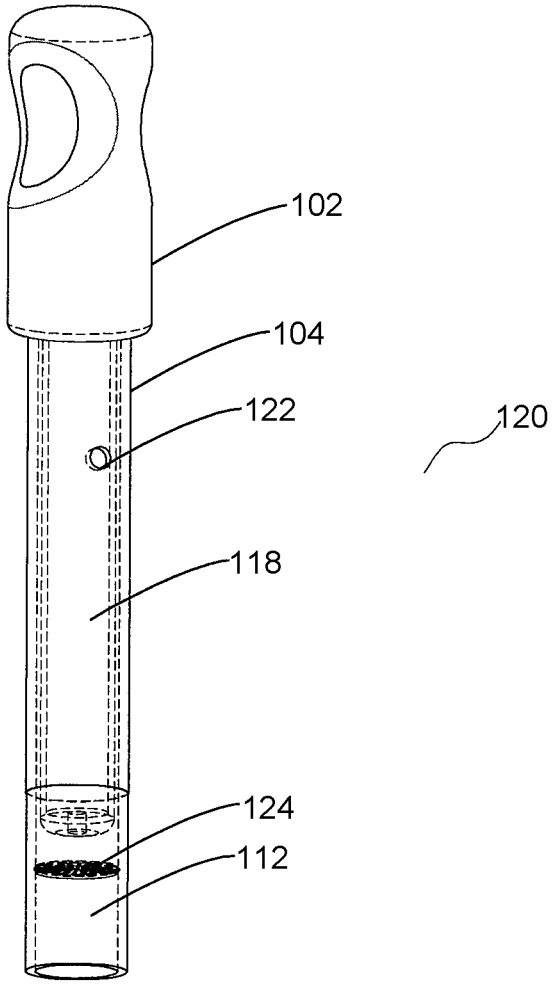
FIG. 6 is a perspective view of another embodiment of a counter flow design exothermal vaporizer shown in FIG. 5 without the cap, in various embodiments, as disclosed herein.
Figure 7:
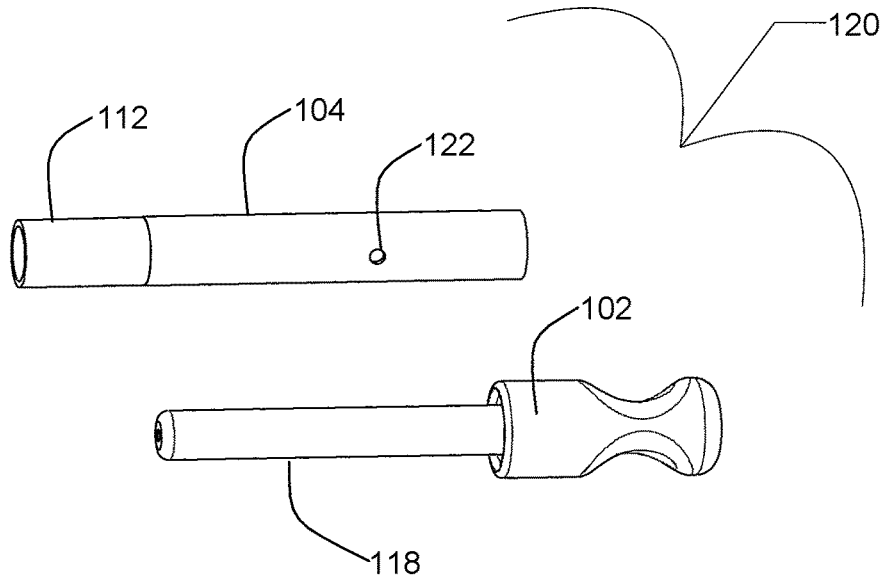
FIG. 7 is a partially exploded perspective view of the exothermal vaporizer shown in FIG. 6, in various embodiments, as disclosed herein.
Figure 8:
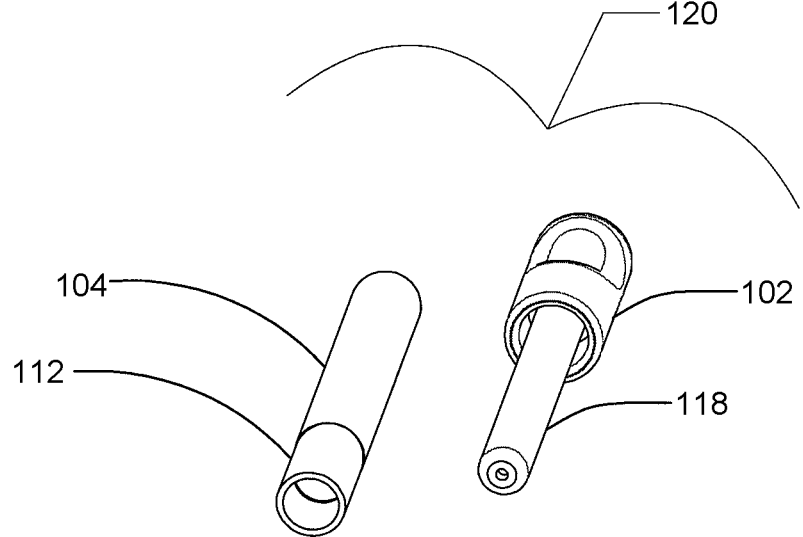
FIG. 8 is an alternative partially exploded view of the exothermal vaporizer shown in FIG. 6, in various embodiments, as disclosed herein.

In one or more examples of embodiments, the exothermal vaporizer is a novel type of vaporizer designed, in various embodiments, for use with existing fluids intended for use with e-cigarettes and other electronic vaporizers. The exothermal vaporizer does not contain any electronic components. It is also much more compact than currently available electronic devices. In various embodiments, the device may be approximately 3.5 inches long and weigh only approximately ¼ oz. However, one of skill in the art would appreciate that variations thereon may be made to suit the desired purposes, as well as to suit a desired look and feel. FIGS. 1-3 illustrate various embodiments of the exothermal vaporizer 100. FIG. 1 demonstrates the various components of the device. As can be readily ascertained in FIGS. 1-3, and in particular FIG. 1, the exothermal vaporizer device 100 may be generally divided into three sections: a mouthpiece 102, a body 104 or stem, and a cap 106, which may be a temperature indicating cap. The body 104 contains or has a number of features, including: an air/vapor mix port 108, a fluid inlet port 110, a reservoir 112, an air inlet 114, and wicking material 116.

As indicated, the exothermal vaporizer 100 includes a cap 106 which is removable from the body 104. The cap may be a temperature indicating cap 106. A suitable temperature indicating cap 106 is described in U.S. patent application Ser. No. 14/142,351, published a U.S. Patent Publication No. 2014/0186015 A1, the entire contents of which is hereby incorporated by reference herein in its entirety. The temperature indicating cap 106 is calibrated to indicate or provide an alert at the ideal vaporization temperature for the fluid or smoking material the exothermal vaporizer 100 is intended to use.

As indicated, the body 104 or stem includes a reservoir 112 or tip. According to one or more examples of embodiments, the reservoir 112 or tip may be hollow such that it may be filled with or contain a vaporizing fluid or smoking material. In various embodiments, the reservoir 112 may be constructed out of glass or any other substance or material suitable for its intended purposes. The fluid/smoking material (not shown) is contained in an internal reservoir, which may feed a wicking material 116 or evaporation matrix contained in the end of the body 104 or tip 112 and may be covered by the temperature-indicating cap 106. In various embodiments, the wicking material 116 is made from any suitably heat resistant wicking material, for example, stainless steel or other metal mesh. Variations thereon are also contemplated. The vaporization chamber 158 is formed by the space at the end of the body 104 covered by the cap 106 during operation, which also contains the wicking material 116 and/or evaporation matrix. The fluid meters into the wicking material 116 by capillary action and/or may also be metered out of the reservoir 112 by pressure fluctuations created by the thermal cycling of the device during and between uses. The temperature rise of the device, due to the heat input required for vaporization, causes an increase in the air pressure present in the fluid reservoir 112. This increased pressure may be utilized to assist in the dispensation and/or metering of the fluid from the reservoir 112 into the wicking element. As the device cools, the air in the reservoir 112 contracts and additional air is drawn into the reservoir 112 to replace the dispensed fluid.

As can be seen in FIGS. 1-3, there are three (3) holes or apertures apparent in the body 104. The holes are longitudinally spaced along the length of the body. The first hole or aperture is the primary air inlet 114 and is located near the cap 106. The second hole or aperture is the reservoir fill hole 110. The third hole or aperture is the dilution air hole(s) 108 used to adjust air/vapor mix and tune the performance of the device to the user's preference. While three holes or apertures are specifically described, it is contemplated that more or fewer apertures may be used to accomplish the purposes provided.

A central tube or condenser 118 is also provided within the body 104. As can be seen in the Figures, the condenser has a smaller diameter than the body and provides an air flow gap between the interior surface of the body and the exterior surface of the condenser. The condenser tube 118 performs several functions. It serves to create the internal side of the fluid reservoir 112, a conduit for vapor extraction, and a means of redirecting vapor condensed in the mouthpiece area back to the wicking material 116. The condenser tube 118 may be constructed of any suitable material for withstanding heat and performing the functionality disclosed herein; for example, but not limited to, glass, stainless steel, or titanium, and combinations thereof.

The mouthpiece 102 is coupled to the body 104 and functions as the interface between the exothermal vaporizer device 100 and the user. The mouthpiece 102 also operates as a valve for the fluid reservoir fill port 110 and air/vapor mix and/or dilution inlet(s) 108. Specifically, an elastomeric mouthpiece 102 may be provided, coupled in a tight sealing fit over the body 104 (at an end thereof) and the corresponding ports. This is accomplished via a manner of a conformable slide valve. While a specific example is provided, it is also contemplated that the mouthpiece 102 or a portion thereof may fit or tightly fit within the end of the body 104. The mouthpiece 102 may be formed of any suitable material, examples of which include, but are not limited to, plastic, rubberized material, glass, metal, wood, and the like, as well as combinations of the foregoing.

The exothermal vaporizer 100 functions to vaporize the fluid contained in the wicking element or material 116 and indirectly from the fluid reservoir 112. Any suitable external heat source (not shown) is used to heat the vaporization chamber (described above) located underneath or enclosed by the cap 106 to the appropriate temperature. The appropriate temperature is indicated by a calibrated thermo-activated element contained within the cap 106.

In one or more examples of use of the exothermal vaporizer 100, a user may first load or fill the device with a substance for vaporization and consumption. Next, the user may apply a heat source, such as a lighter, to the base (i.e., the downward facing portion of the vaporizer 100 when held by the user) of the device. A metal temperature sensor or thermo-indicator may then indicate to the user the substance is ready for consumption. Next, the user may apply suction to the mouthpiece 102 to consume the substance. This suction creates a pressure drop in the vaporization chamber (described above) forcing air into the air inlet hole 114, then through or around the evaporation matrix or wicking material 116 followed by a 180 degree change in direction going up through the central tube/condenser 118 to the mouthpiece 102. As the vapor flow enters the mouthpiece area it is diluted by the dilution air via the air/vapor ratio port 108 to the user's preference. The user may then inhale the mixed air and vapor. Vapor production will diminish as the temperature drops in the vaporization chamber. Shortly afterwards the temperature indicator may indicate it has cooled sufficiently and reset and is now ready for another heating cycle.

One or more alternative examples of embodiments of an exothermal vaporizer 120 having a counter flow design are shown in FIGS. 4-8, which illustrate various embodiments of the device. Like the exothermal vaporizer 100 described hereinabove, the counter flow exothermal vaporizer 120 shown in FIGS. 4-8 may, in various embodiments, be approximately 3.5 inches long and weigh only approximately ¼ oz. However, variations thereon would not depart from the overall scope of the present invention.

Various elements of the exothermal vaporizer 120 shown in FIGS. 4-8 are substantially similar to the elements shown and described in FIGS. 1-3 and therefore like numbers will be used to identify like components. The exothermal vaporizer 120 shown in FIGS. 4-8 incorporates several additional elements. First, a ventilation hole or holes 122 are positioned near the mouthpiece 102. Next, the internal condenser tube 118 is installed running or extending the length or approximate length of the device 120 from the mouthpiece 102 stopping or terminating just short of a diffuser disc 124. The mouthpiece 102 or O-ring(s) 126 retain(s) the condenser tube 118 in place.

In one or more examples of embodiments, the device may also include, or fit within a housing or other container for safety and portability.

The above described combination of elements of the exothermal vaporizer 120 of FIGS. 4-8 includes several features. First, it provides or has a tighter fit of the cap 106 relative to the body 104, which improves conducted heat transfer and helps retain the cap 106 in the correct position both during use and non-use. Second, a significant proportion of the airflow through the device is a bypass of the extraction chamber. Consequently, there are several benefits, including, but not limited to: extended time at operational temperature; reduced extract concentration; reduced effort to draw or minimized suction to use the device; and lowered extract temperature. Third, the condenser tube 118 re-directs airflow and creates a wash of the interior surface of the outer tube (i.e., body 104) as the dilution air entering the device near the mouthpiece 102 travels toward the chamber end carrying any errant vapor with it where it then has to make a 180 degree turn to enter the condenser tube 118. This dilution air reduces the accumulation of plant matter and condensates on the interior surface of the outer tube 104. The 180-degree turn and corresponding acceleration in velocity of the dilution air stream also creates a localized drop in air and vapor pressure adjacent to the extraction chamber. This promotes the extraction and evacuation of the extracted compounds from the sample. Next, since the condenser tube 118 has a smaller cross-sectional area and diameter than the body 104, the same volumetric flow of dilution air and vaporized extract is now accelerated to a much higher velocity as it transits the device. This, in conjunction with the substantially smaller surface area of the condenser tube 118, minimizes the amount of vaporized material condensed out of the air/vapor stream. In addition, the incorporation of the dilution air reduces the level of saturation in the vapor stream promoting the retention of the liberated compounds in the air/vapor stream for improved ingestion and absorption. This process also lowers the temperature of the air/vapor stream which reduces the harshness or irritation and/or coughing associated with pulmonary irritation caused by high temperature gases and aerosols such as smoke.

The disclosed improved device also allows for easier cleaning. For example, the condenser tube 118 provides for an easier way to remove accumulated residues from the device following extended usage. In particular, the mouthpiece 102 or O-ring(s) 126 retain(s) the condenser tube 118 in place, so the condenser tube is easily removed. Accordingly, all of the components are accessible and easy to clean, remove and/or replace.

FIGS. 9-16 demonstrate one or more additional and alternative examples of a exothermal vaporizer 130. Various elements of the exothermal vaporizer 130 shown in FIGS. 9-16 are substantially similar to the elements shown and described in FIGS. 1-8 and therefore like numbers will be used to identify like components. However, the vaporizer 130 shown in FIGS. 9-16 includes a number of additional features, including: a condenser tube 132 comprised of titanium, stainless steel, or another suitable material or combinations of materials, a condenser 132 which has threads and may thread into the mouthpiece 136 (having corresponding mating threads) and is adjustable to modulate and/or regulate the flow ratio of dilution air and produced vapor, integration of the tip 134 and the mouthpiece 136 into the body 104 with friction fit O-rings 126 (allowing for tool-less assembly and disassembly, as well as thermal isolation of, among other things, the tip 134 from the body 104), a variety of material choices for the components with a standardized interface size, and strategic material use across the device.

Figure 9A:
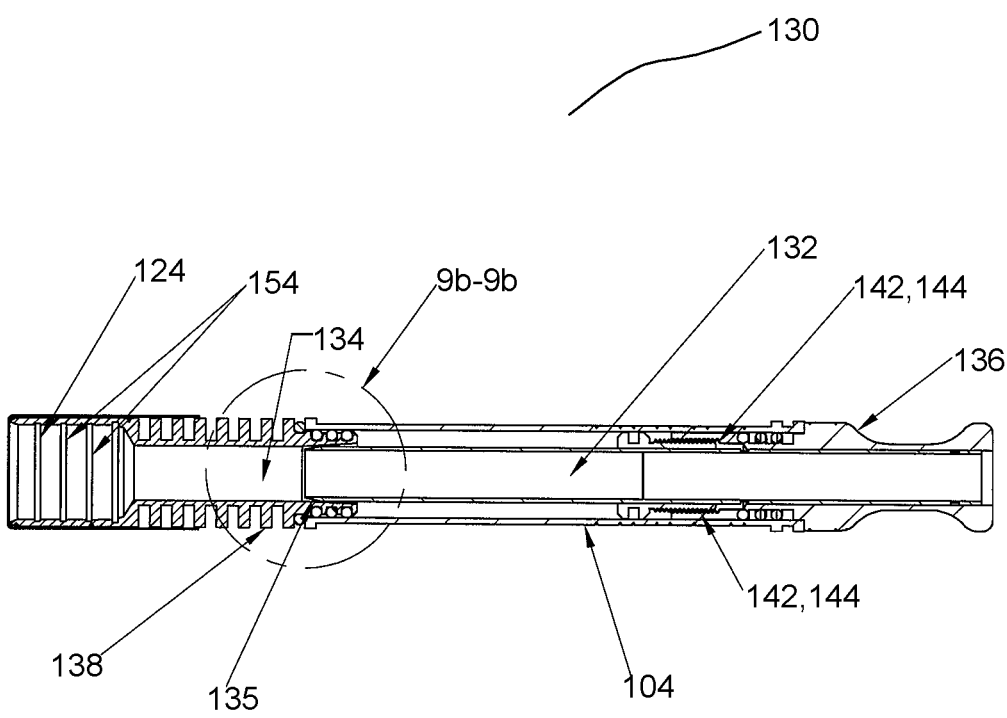
FIG. 9a is side elevation cross-sectional view of a modular exothermal vaporizer, according to various embodiments.
Figure 9B:
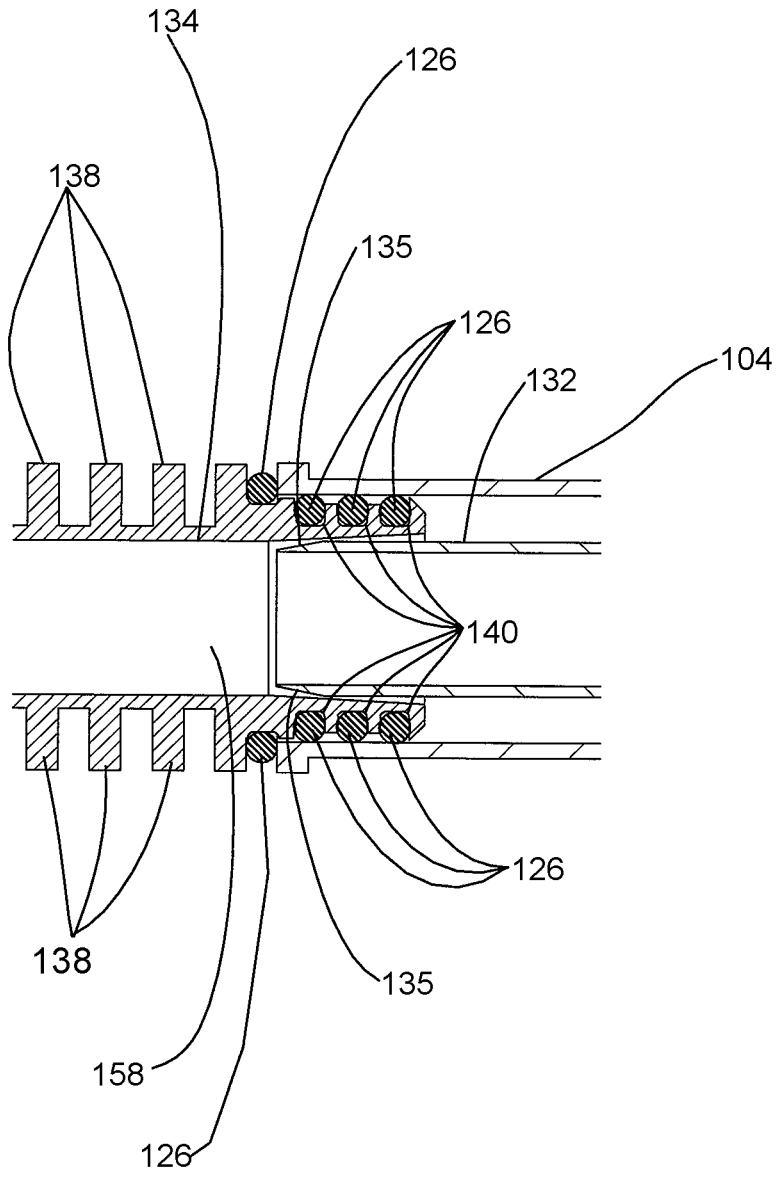
Figure 9C:
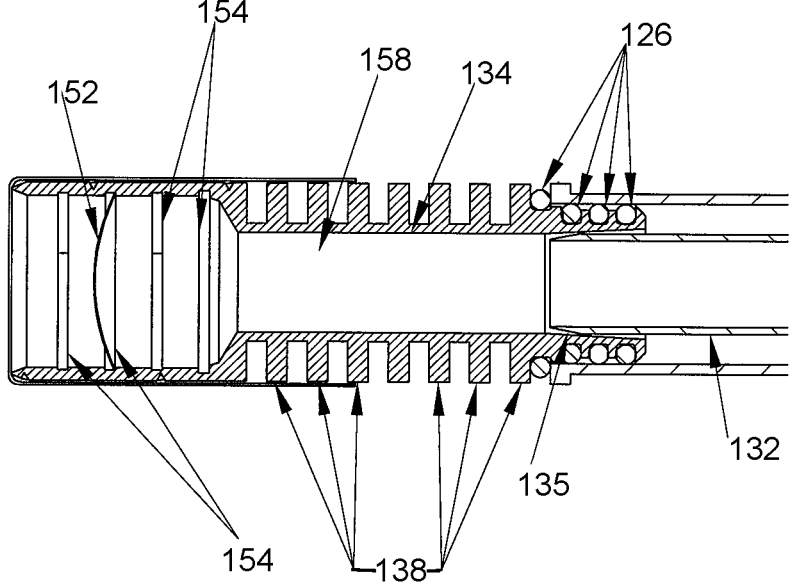
FIG. 9c is a side elevation cross-sectional view of a portion of the modular exothermal vaporizer of FIG. 9a, including an alternative example of a tip and diffuser disc.
Figure 10:
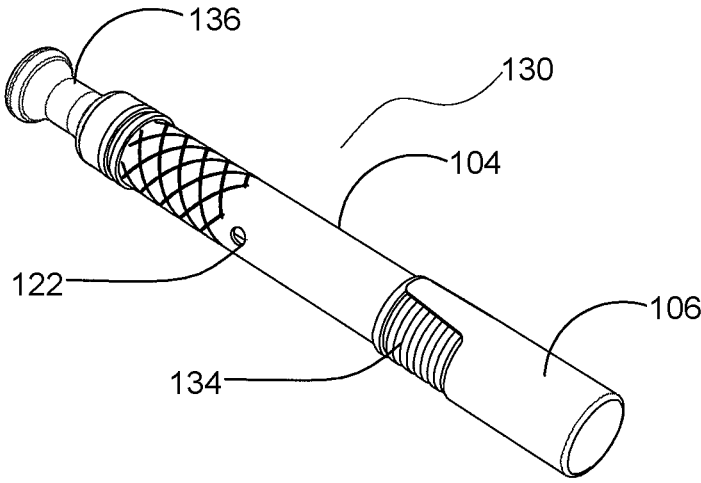
Figure 11:
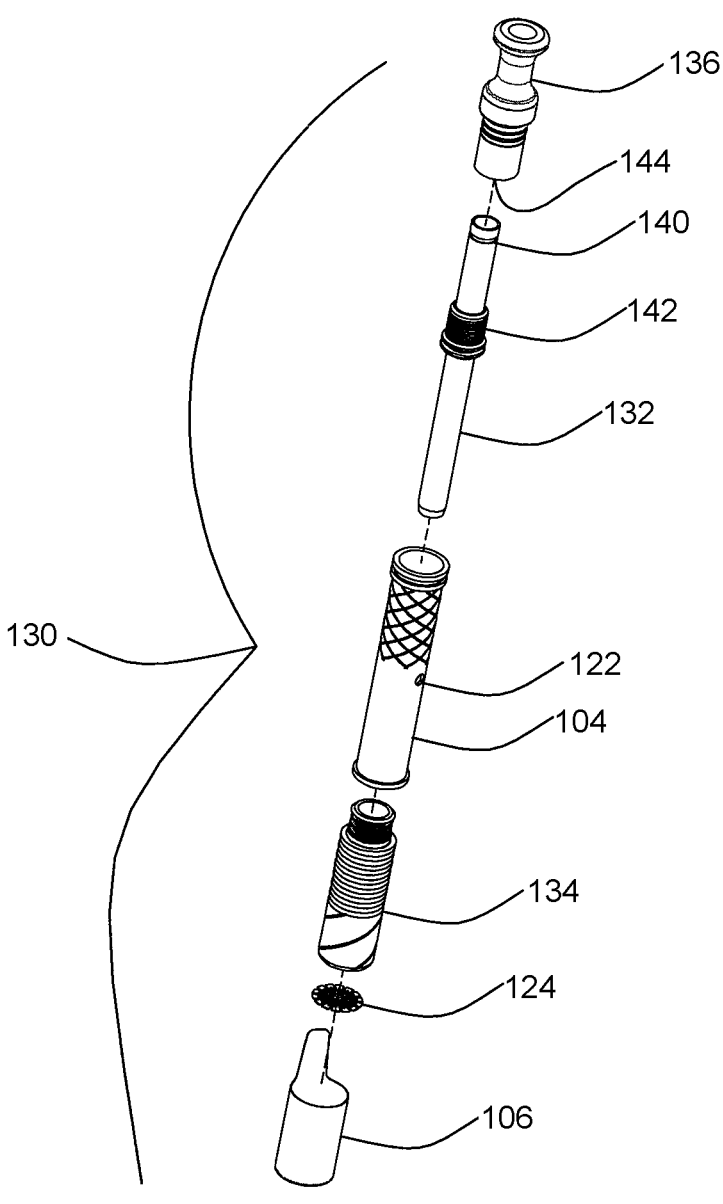
FIG. 11 is an alternative perspective exploded view of a modular exothermal vaporizer according to one or more examples of embodiments.
Figure 12:
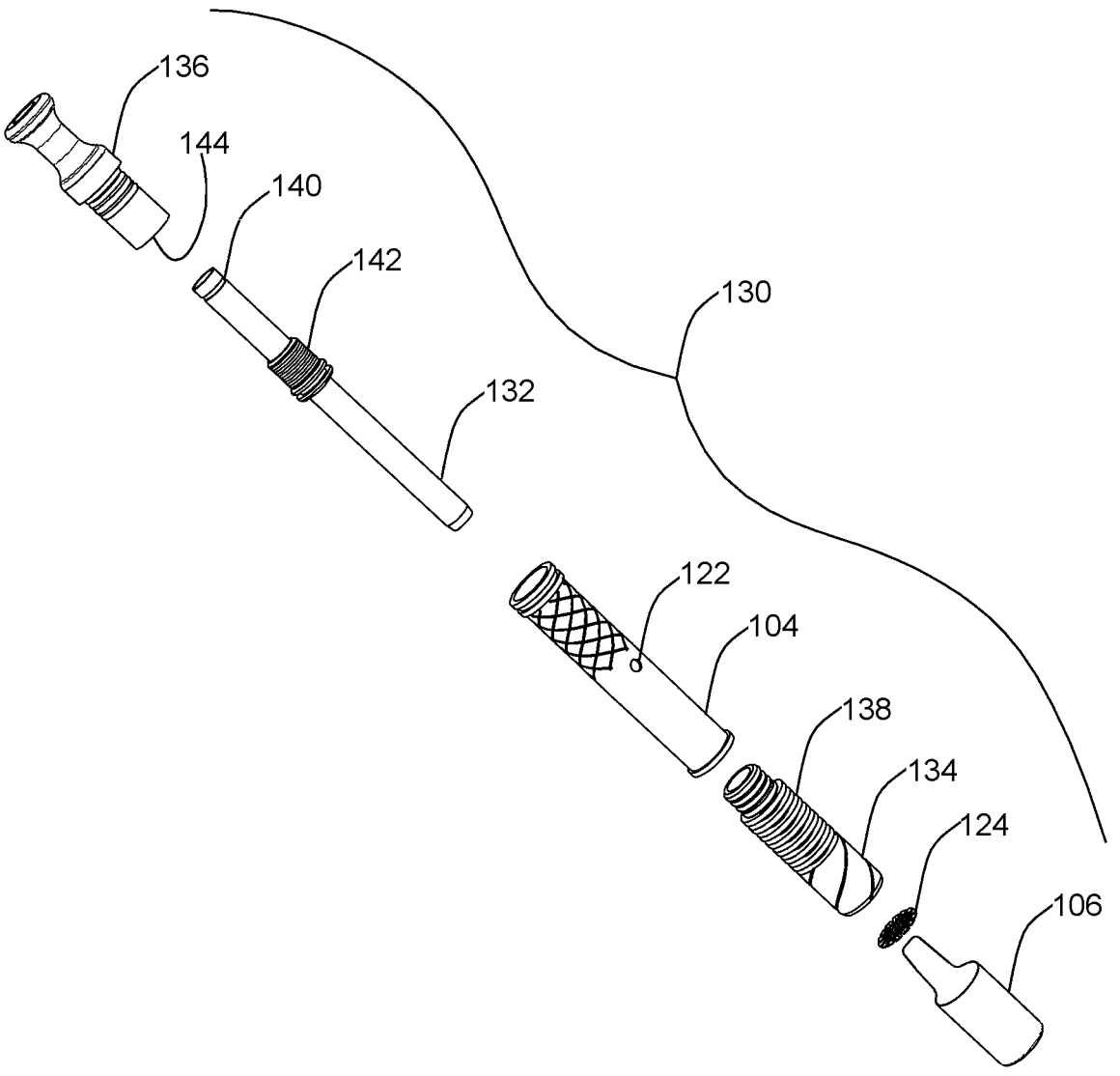
FIG. 12 is an alternative perspective exploded view of a modular exothermal vaporizer according to one or more examples of embodiments.
Figure 13:
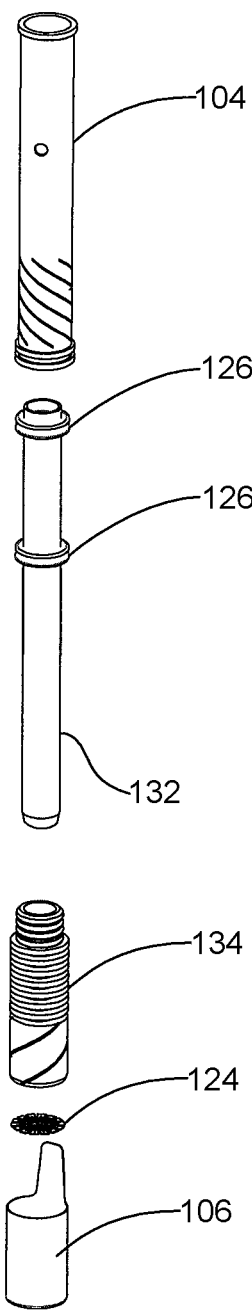
FIG. 13 is an alternative perspective exploded view of a modular exothermal vaporizer according to one or more examples of embodiments, with no mouthpiece shown.
Figure 14:
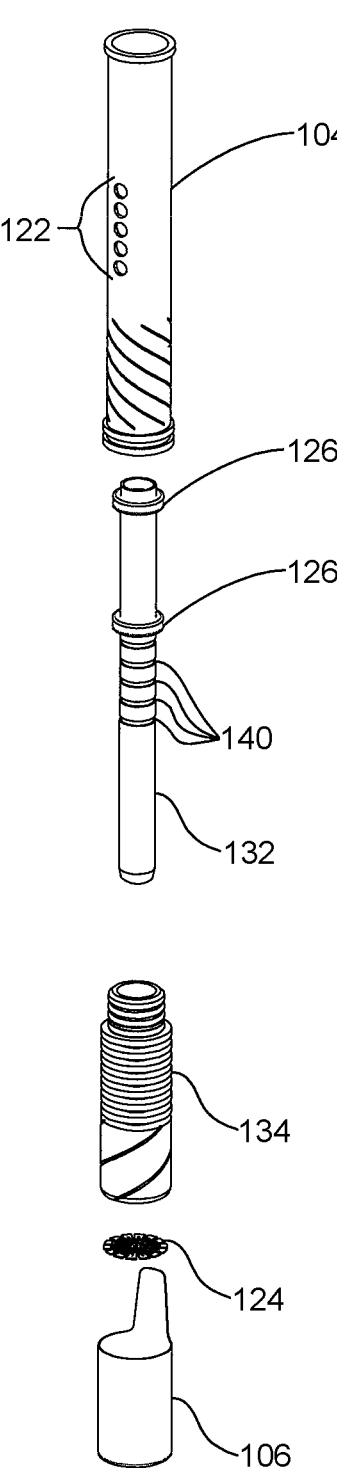
FIG. 14 is an alternative perspective exploded view of a modular exothermal vaporizer according to one or more examples of embodiments, with no mouthpiece shown.
Figure 15:
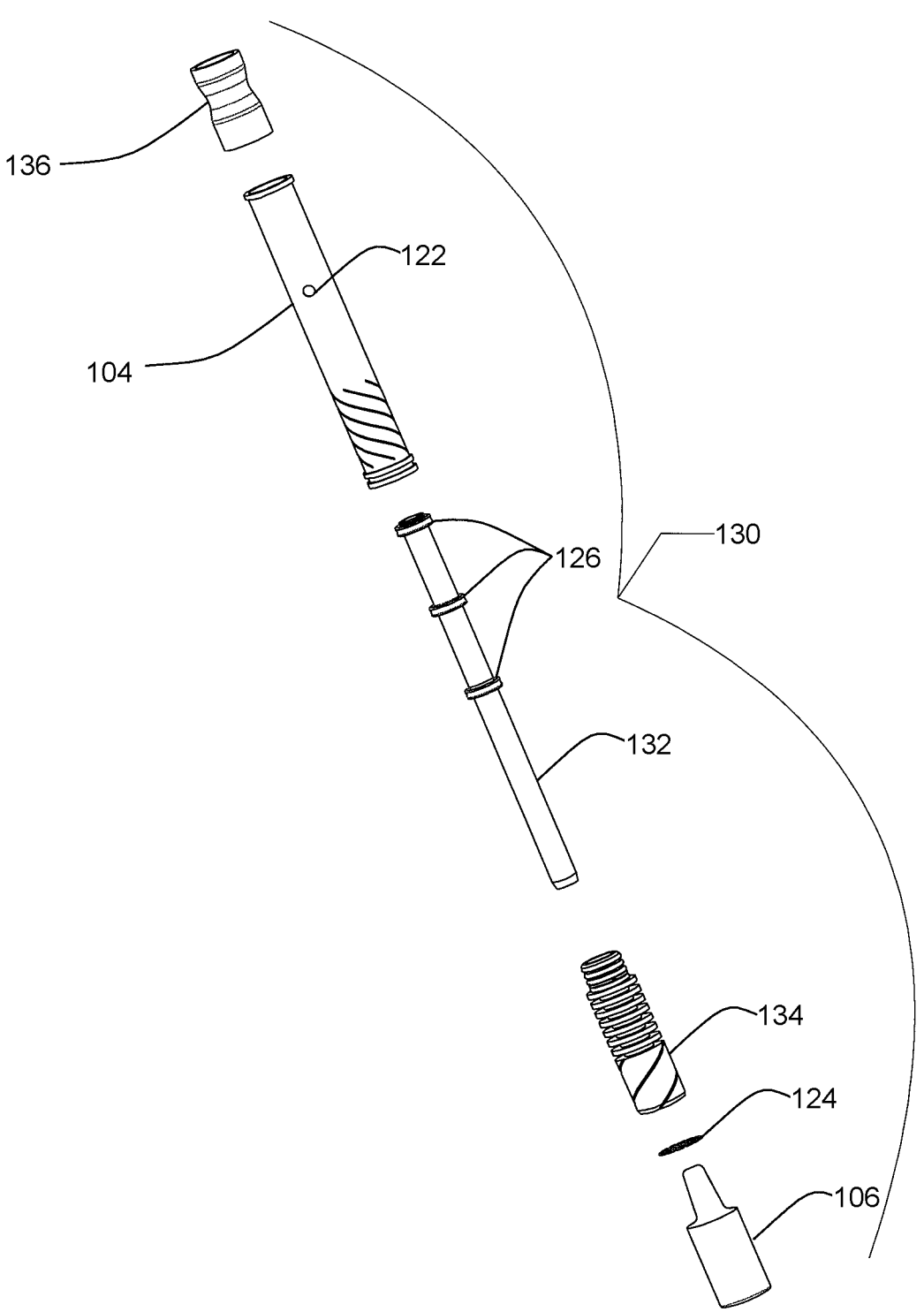
FIG. 15 is an alternative perspective exploded view of the modular exothermal vaporizer shown in FIG. 13, including the mouthpiece.

FIGS. 9a-c illustrate cross-sections of a modular exothermal vaporizer 130, according to various examples of embodiments. The assembled vaporizer is shown in FIG. 10. Referring to these Figures, various parts of an exothermal vaporizer 130 are disclosed. A tip 134 for the exothermal modular vaporizer 130 is shown which couples and/or interfaces with/to a condenser tube 132. As indicated above, the condenser tube has a smaller diameter than the body and when inserted into the body provides an air gap between the exterior surface of the condenser tube and the interior surface of the body. In various embodiments, the condenser tube 132 is optimized for communication with the tip 134 for flow modulation. For example, the tip 134 and/or condenser 132 may have a taper 135 at the interface for flow modulation. As can be seen in the Figures, the taper 135 is a very small/short decrease in external diameter of the condenser 132 at the very end or interfacing surface of the condenser adjacent the tip interfacing surface.

A heat dissipation feature 138 is also shown in FIGS. 9-10, which may, in various embodiments, be in the form of fins—which aid in heat dissipation. For example, the fins 138 make the conductive path smaller by minimizing the cross-sectional area as well as providing an increased surface area for dissipation of errant heat conducted away from the vaporization chamber 158. The fins 138 or other features may also function to assist in heat transfer to preheat incoming vapor displacement air. This function also has the added benefit of cooling the end of the tip 134 where it joins the body 104, minimizing the transfer of heat from the tip 134 to the body 104 in the process of recycling the heat conducted away from the vaporization chamber 158 otherwise lost back into the incoming airstream preheating it to further reduce the rate of heat loss in the vaporization chamber due to the incoming air.

As can be seen in reference to the Figures and discussed in further detail hereinbelow, the exothermal vaporizer 130 components may have grooves 140 which are suitably sized to accept O-rings 126. O-rings 126 may be formed of silicone, FKM or Viton™, or other suitable thermally-isolating material (described in further detail below). In addition, threads 142 may be provided on the condenser tube 132 spacing relative to the tip 134. This feature, in various embodiments, allows for adjustment of airflow relative to vapor production into the vaporizer 130 condenser tube 132.

Referring to FIG. 9c, in one or more alternative examples of embodiments, a bowed or domed screen or diffuser disc 152 may be provided in the tip 134. The tip 134 may have multiple grooves 154 (also shown in FIG. 9b) for adjusting the size of the vaporization chamber 158 (discussed in further detail hereinbelow in reference to FIGS. 17-22). In the illustrated embodiment four (4) such grooves are shown, although one of skill in the art would appreciate the more or fewer such grooves 154 may be provided without departing from the overall scope of the present invention. In one or more examples of embodiments, the screen 152 is press-fit into the tip. In this regard, the screen 152 may be provided with circumferential compression, and when in combination with its insertion into a groove, it resists force thereby retaining the screen in the tip.

The foregoing configuration advantageously provides for optimal heat management, containment and controlled dissipation.

A variable ratio flow control may also be provided. For example, adjustment of the ratio between direct vapor chamber flow through and inverse induction dilution air is accomplished by rotating the mouthpiece 136 relative to the body 104 of the vaporizer 130, which threads or unthreads, withdrawing or extending the condenser tube 132 from the mouthpiece 136 and changing the interfacing clearance between the condenser tube 132 and the tip 134, or otherwise modifying and/or modulating the restriction in the dilution air flow path.

As can be seen in reference to FIGS. 9a-c, a tapered condenser tube 132 (see taper 135), or other flow modulation component, is actuated via the twisting of the mouthpiece 136 relative to the body 104 in order to modulate flow control. In various embodiments, this feature is facilitated by the engagement of the threads 142 provided on the condenser tube 132 with the corresponding mating threads 144 incorporated into the mouthpiece 136 to adjust the condenser tube 132 spacing relative to the tip 134. Accordingly, the physical action used to facilitate this adjustment is a twisting motion. In other words, a user may twist or untwist the mouthpiece 136 relative to the body 104, which may then facilitate the actuation of the condenser tube 132 relative to the mouthpiece 136, body 104, and/or tip 134. While a specific example is provided, other means of adjusting and/or regulating the ratio of air induction in order to optimize vapor concentration (flow modulation) may also be provided, e.g., sliding vs. twisting, or other similar methods of engaging one or both sides of the condenser and its mating component(s). In the embodiment described, the condenser tube 132 remains rotationally fixed relative to the body 104 as the mouthpiece 136 is twisted. The twisting of the mouthpiece 136 threads or unthreads the condenser tube 132, actuating it either towards or away from a valving or restriction point. This enables "dialing in" or modification of the vapor and dilution air mixture. In other words, in various embodiments, the internal or external dimension of the condenser tube 132 and/or interfacing aperture of the tip 134 or body 104 of the vaporizer 130 tapers or has a taper 135 to act as a needle valve and seat for adjusting and modulating flow and moderating the air and vapor ratio.

The flow modulation may occur at the internal interface between the condenser tube 132 and the tip 134 (which includes the extraction chamber). Accordingly, the tip 134 may have an inside diameter slightly larger than the condenser tube 132. In addition, the tip 134 and/or the condenser tube 132 may have one or more interfacing surfaces.

These interfacing surfaces may have a taper incorporated and geometry to provide an incremental increase and/or decrease in an aperture provided between the tip 134 and the condenser tube 132 upon extension and/or retraction relative to one another. The variable aperture provides a means of regulating and/or modulating the ratio between produced vapor and/or dilution air. For example, as a user inhales, vapor is displaced from the extraction chamber by incoming air and condenser tube 132 through the tip 134 (by way of the diffuser). In addition, dilution air can enter the extraction chamber by way of a space (aperture) provided, in various embodiments, between the body 104, condenser tube 132, and mouthpiece 136. In addition or in the alternative, an aperture 146 may be provided in the body 104. While specific examples are described, additional means of either restricting the dilution air and/or promoting the vapor production and/or flow in a user-adjustable fashion would also be considered within the scope of this disclosure.

In addition to the foregoing, the user adjustable variable air/vapor ratio may be used with both liquid vaporizers and other smoking material (e.g., dry herb or plant) vaporizers. For example, an adjustable variable air/vapor ratio may function via a similar user actuated valving and ratio adjustment system. In one embodiment this feature may be accomplished via twisting the mouthpiece 136 portion of the vaporizer 130 relative to the body 104, which facilitates the extension and or retraction of the condenser relative to the tip 134 valving modulation. This valving may be accomplished by having a threaded portion of the inner or condenser tube 132 threaded into the mouthpiece 136, therefore when the mouthpiece 136 is rotated relative to the condenser tube 132, the condenser tube 132 is then either extended or withdrawn from/into the mouthpiece 136.

As indicated above, the flow modulation may occur at the internal interface between the condenser tube 132 and the tip 134 (which includes the extraction chamber). The tip 134 may have an inside diameter slightly larger than the condenser tube 132 and either the tip 134 or the condenser tube 132 or both have a taper incorporated into their respective interfacing surfaces and dimensions to provide an incremental increase and/or decrease in aperture upon extension and/or retraction relative to one another. It is this variable aperture, which may be responsible for one described means of regulating and/or modulating the ratio between produced vapor and/or dilution air.

Additional means of modulating the flow can be created by drilling holes or other apertures arranged in a linear (or other suitable) fashion from the mouthpiece 136 towards the vapor chamber. It is the arrangement or pattern of said apertures when in one embodiment an internal seal or other slidable valving mechanism is actuated across the apertures. As more apertures are isolated from the air induction side of the seal or valving mechanism, the induction air flow may be modulated and/or restricted. The movable seal or valving mechanism may be adjusted via a threaded extension/retraction mechanism actuated by twisting the mouthpiece 136 against the body 104.

Another embodiment or means for modulating the flow may include a series of grooves 140 on the condenser tube 132 to retain a slidable and repositionable seal such as an O-ring 126. This arrangement may allow the user to modulate and adjust the device to their preference of extraction strength and vapor temperature by selecting different seal positions relative to the condenser tube 132 and its position when retained in the body 104. The grooves 140, although useful for retaining the seal(s) may not be required or necessary in various embodiments. In various embodiments, means required for modulation in this arrangement may include the ability to seal against or isolate from the induction airflow any number of the apertures in the body 104 which would allow air to enter the interstitial space between the condenser tube 132 and the inside of the body 104 thereby modulating the air flow.

Another embodiment of or means for modulating flow may include valving or otherwise restricting the apertures from the external side of the condenser 132. This may be accomplished via a component of the device or a separate device, including the operator's fingers.

Another embodiment or means for modulating flow or of air/vapor adjustment may include a user adjustable spring tension against a valving mechanism. This may allow for a real time functioning of a flow and pressure-regulating device which can compensate air and/or vapor flow during use based on the pressure differential created during use. This feature may allow the user to simply adjust the strength of the vapor concentration extracted instantly by increasing and/or decreasing the applied suction to the mouthpiece 136.

While various examples are specifically provided, another or additional means of either restricting the dilution air and/or promoting the vapor production in a user adjustable fashion may also be considered within the scope of this disclosure.

As shown in FIGS. 9-16, the exothermal vaporizer 130 as disclosed herein may be modular. The manner in which the condenser 132, tip 134 and other interfacing elements connect, actuate and the corresponding clearances allow for interchangeability of components and use of multiple material types including materials which would otherwise be unsuitable if they were directly connected without a thermal break. In order facilitate a tool-less friction fit incorporation of an element or component it is preferable to hold a tight dimensional tolerance to ensure the correct amount of elastomeric deformation and/or compression needed for retention of the component with its corresponding parts.

In FIGS. 9-16, a tip 134, diffuser 124, body 104, and mouthpiece 136 of the exothermal modular vaporizer 130 according to various examples of embodiments are provided. The condenser tube 132 is provided within the body 104 and mouthpiece 136, which, as indicated above, tapers towards the tip 134 for interaction with the tip (and diffuser 124). The tip 134 is separable from the body 104 and the mouthpiece 136 is separable from the condenser 132.

Figure 16:
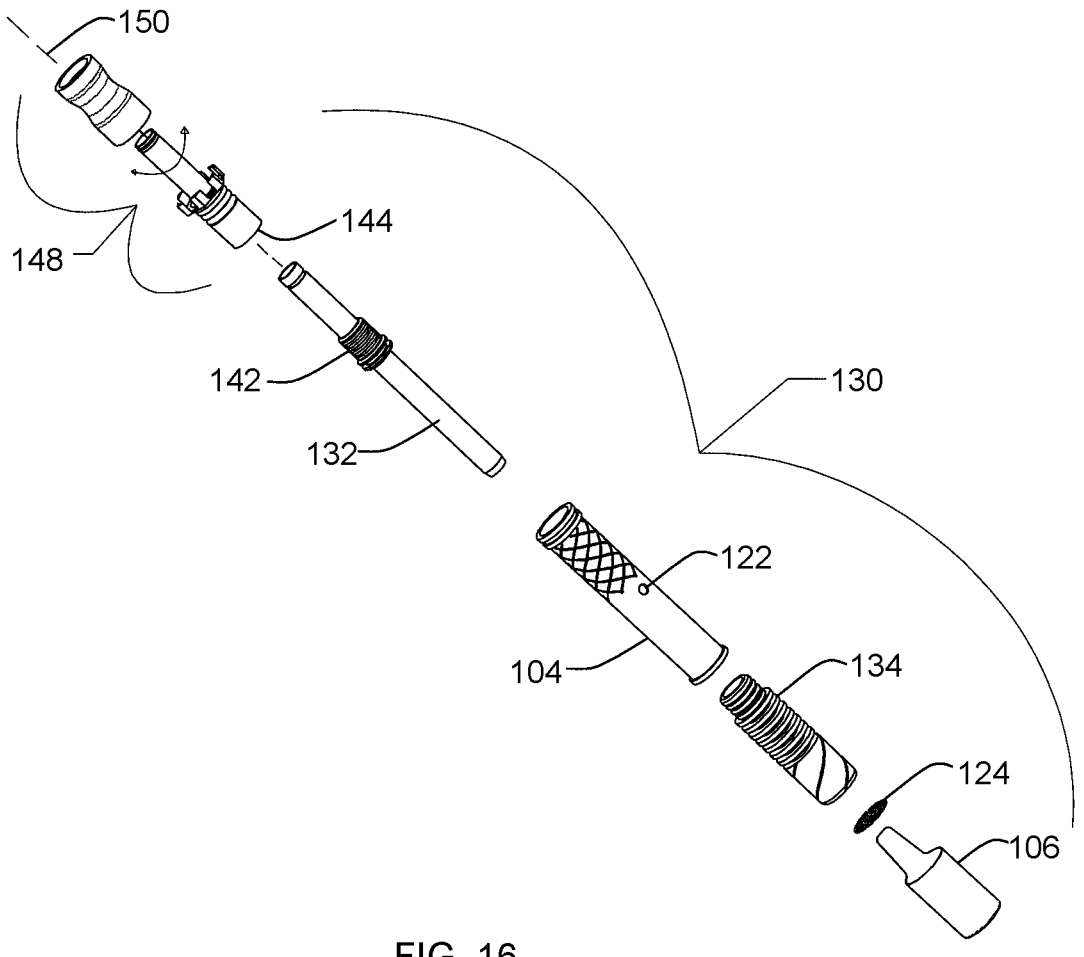
FIG. 16 is an alternative perspective exploded view of a modular exothermal vaporizer according to one or more examples of embodiments, and including a rotating or spinning mouthpiece.
Figure 17:
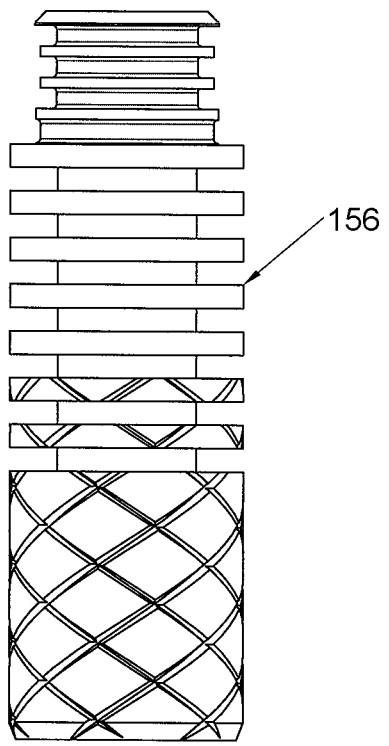
FIG. 17 is a plan view of one or more alternative examples of a tip for use with an exothermal vaporizer as described herein.
Figure 18:
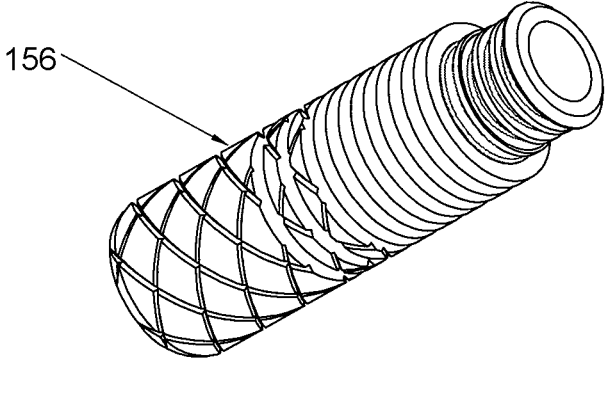
FIG. 18 is a perspective view of the tip shown in FIG. 17.
Figure 19:
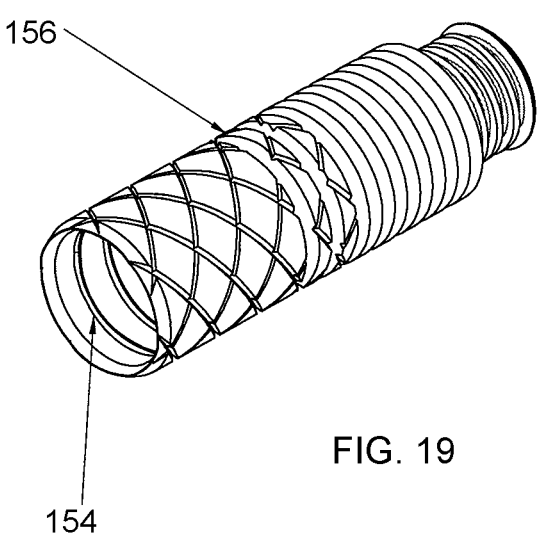
FIG. 19 is an alternative perspective view of the tip shown in FIG. 17.
Figures 20, 21:
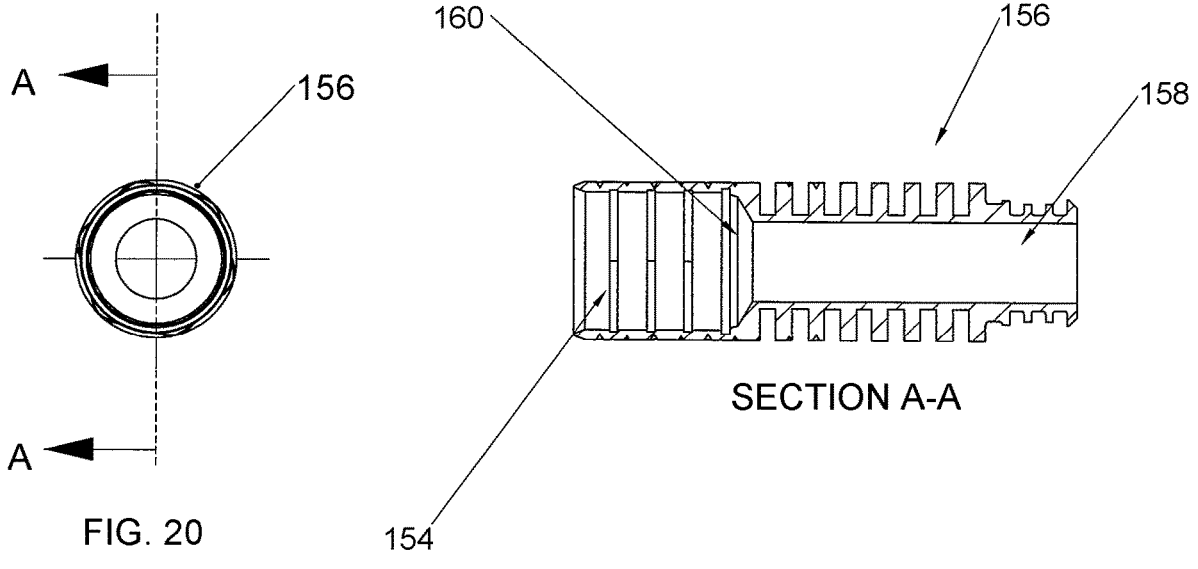
FIG. 20 is an end elevation view of the tip shown in FIG. 17.
FIG. 21 is a cross-sectional view of the tip shown in FIG. 17, taken from line A-A of FIG. 20.
Figure 22:
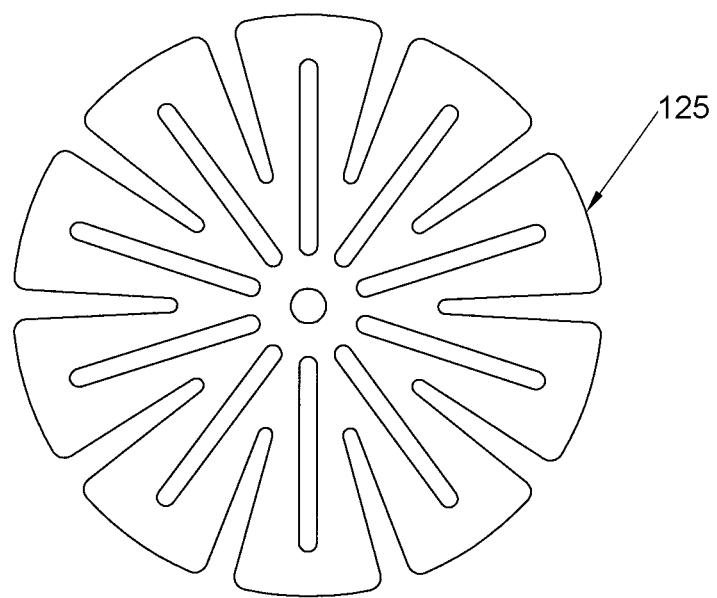
FIG. 22 is a plan view of a screen or diffuser disc for use with the tip shown in FIG. 17 according to one or more examples of embodiments.

In one or more examples of embodiments shown in FIG. 16, the mouthpiece or a portion thereof may be a rotating or spinning mouthpiece 148. For example, the mouthpiece in one example of embodiments freely rotates 360 degrees. That is, the mouthpiece or mouthpiece portion 148 (or conversely the body 104 or a component thereof) may rotate about an axis 150 such that the body 104 can be rotated relative to the mouthpiece 148 for even heat application. In one example of embodiments, the mouthpiece 148 may be incorporated or otherwise attached to the vaporizer 130 via a coaxial engagement with the condenser tube 132 running through the diameter of the mouthpiece—with the mouthpiece held in place by O-rings 126 affixed to the condenser 132 at either end of the mouthpiece 136. This arrangement provides for retention of the mouthpiece 148 while also allowing for free rotation about the condenser tube 132.

The modularity is assisted by a friction fit assembly provided by O-rings 126 provided within grooves 140 on the vaporizer 130. The grooves 140 may be provided, in various embodiments, on the tip 134, condenser tube 132, and/or mouthpiece 136, however, variations thereon accomplishing the purposes provided may also be acceptable.

In various embodiments, five to eight O-rings 126 may be provided on the various parts of the vaporizer 130. In one or more particular examples of embodiments, the O-rings 126 may be coupled together in a pattern, for example in a double O-ring pattern, to enhance functionality. However, any number of O-rings 126, or other types of retaining rings may be provided to suitably achieve the effects disclosed herein. In various embodiments, recesses or grooves 140 may also, optionally, be provided on the device to which the O-ring 126 is secured to allow for the O-ring to retain its position on the device through assembly and disassembly, as well as provide a suitable degree of friction-fit and/or anti-rotation resistance. The O-ring 126 configuration may allow for rapid and easy assembly and disassembly without the need for any tools. This feature may be highly desirable to facilitate cleaning of residues from some of the internal surfaces and components.

In various embodiments, O-rings 126 may be provided on an upper surface (i.e., near the mouthpiece) of the vaporizer 130 acting as a frictional element instead of a seal. For example, an O-ring 126 may be used on the condenser tube 132 to maintain the condenser tube 132 in a rotationally fixed position relative to the body 104, yet still allow for axial movement. In various embodiments, this feature may act as a higher level of friction compression fit, which resists rotation of the body 104 during "dialing-in" or adjustment of the condenser tube 132 relative to the tip 134.

The O-ring 126 thickness may be suitably sized to resist the unintended disassembly of the vaporizer 130 yet allow for easy intentional disassembly of the vaporizer 130. Suitable examples of friction fit O-rings 126 include 6 mm I.D×1 mm cross-section O-rings, yet any suitable combination of sizes may be used provided the O-ring provides the required interference fit necessary for the retention of the components. The O-rings 126 may be comprised of any suitable material, one example of which is silicone. Other suitable materials may include Teflon™, Viton™, or any other material which allows for maximum temperature of over 400 degrees F.

In this regard, in addition to the friction fit the O-rings 126 provide an insulative interface between heated and/or hot components and unheated components or components which perform better or more comfortably when cool. Accordingly, the O-rings 126 preferably have a thermal conductivity substantially lower than the components they are retaining and act to separate the components of the vaporizer 130 in the manner described herein. This results in a substantially reduced rate of thermal migration from the "hot end" of the device into the cooler regions and/or components. In addition to the thermal isolation, the O-rings 126 also allow for the joining of materials and/or components with substantially different coefficients of expansion.

Accordingly, an advantage of the position, height, and material selected of the O-rings 126 may include thermal isolation of the components of the vaporizer 130. In other words, while normal use of the vaporizer 130 may involve heating the cap 106/tip 134 to a suitably high temperature or degree for vaporization of material provided within the tip 134, a user may continue to hold the body 104 of the vaporizer 130 and consume vapor through the mouthpiece 136 without an uncomfortable transfer of heat from the tip 134 to the remainder of the vaporizer 130. The thermal isolation may be facilitated by the spring back or space provided by the features of the O-rings 126. This may, in various embodiments, eliminate the direct path of conduction and/or heat transfer between the tip 134 and remainder of the vaporizer 130.

In addition, the isolation of the components using the O-rings 126 and grooves 140 may allow for the use of a variety of materials, which may otherwise be incompatible with a vaporizing device. For example, the entire device may be comprised of titanium or other suitable material. This may include ceramic, stainless steel, or nitinol. In other embodiments, the components may be comprised of wood, glass, or any other suitable material. For example, the chamber or body 104 and/or mouthpiece 136 may be in particular comprised of wood or glass, while the tip 134 and/or mouthpiece 136 may be comprised of metal. In another embodiment, the mouthpiece 136 may be comprised of wood, the interior condenser tube 132 comprised of glass, and the tip 134 comprised of metal (including suitably conductive materials including tungsten, gold, titanium, sapphire, etc.). Likewise, one or more components or the entire device 130 may also be formed of a plastic, such as by injection molding or other molding techniques. While specific examples are described, many other suitable combinations and materials may be understood as encompassed within the scope of this disclosure.

While various examples of embodiments include O-ring coupling of the various components of the device, in one or more alternative examples of embodiments, other means may be used to join the components of the exothermal vaporizer 130 disclosed herein. As a non-limiting example, cryo-coupling may be used to couple materials together while avoiding brazing and other mechanisms, which may result in noxious fumes and unwanted metal oxidization or contamination or residues. Cryo-coupling may allow for cooling of various components of the device and assembling the exothermal vaporizer 130 in a limited manner to produce a bond almost as strong as welding. In various embodiments, the device may be manufactured in part by drilling out a bolt such that it fits evenly with the tip 134.

The modular construction and separable/connectable components (including, but not limited to, similar sized features at component interfaces) of the exothermal vaporizer 130 described herein allows for use of a broad range interchangeable components, providing a simple way to upgrade or simply modify the appearance (and in some instances functionality) of the exothermal vaporizer 130 unit depending on the user's preference. This modularity also allows for the incorporation of aftermarket component(s) as a supplement to OEM units (for example, different-shaped components may be used with the disclosed configuration). The modularity also provides an ability to provide an exothermal vaporizer 130 in the form of a kit including one or more of the components described herein, which components may be assembled by a user. For example, a kit may include (but is not limited to): one or more bodies, one or more condensers, one or more tips, one or more mouthpieces, and various O-rings and/or other additional components or fewer components. Each of the components may be of the same material, or may be formed of differing materials as described herein (e.g., a glass body and a titanium body may be provided in a kit or multiple glass bodies may be provided, and so forth). In one or more examples of embodiments, the kit and components thereof may be provided in a container or package containing said components, or multiple containers/packages.

In addition to the foregoing, a glass filter may be provided for use with the exothermal vaporizer 130 in various embodiments. Filter or diffuser discs 124 may be constructed from glass, ceramic or metal, and may be retained by a retaining ring and groove 140 in the body 104 or in another embodiment may be retained in a more permanent fashion by creating a slight depression on the glass body 104 by heating the glass and allowing the depression to encompass both the top and bottom of the disc 124.

As indicated hereinabove, it should be understood the disclosed device, as well as components of the device may be used for traditional smoking purposes. In other words, dried material may be directly placed in the device and burned without the use of the cap 106. To this end, a glass or other type of material screen may be provided on the tube to allow for direct contact between the heating source and dried material.

Referring to FIGS. 17-22, a tip 156 for use with a circumferential compression fit diffuser disc 125 (FIG. 22) is provided. The combination illustrated enables a user adjustable vaporization chamber 158. This is accomplished via grooves 154 in the interior wall of the vaporization chamber 158 into which the circumferential compression fit diffuser disc 125 can integrate. To adjust, the size, the user may push the circumferential compression fit diffuser disc 125 all the way to the bottom of the adjustable vaporization chamber 158, where the groove 160 is deeper to allow for a more complete relaxation of the circumferential compression fit diffuser disc 125 facilitating the inversion of the doming from the insertion. Due to the size of the disc, the doming will always point in the direction the circumferential compression fit diffuser disc 125 is pushed and correspondingly force from the other direction will be resisted. Upon relaxation of the disc into the deeper groove, the circumferential compression fit diffuser disc 125 can be inverted with a tool from the opposite direction, and pushed outward. The circumferential compression fit diffuser disc 125 will click into any of the grooves and be retained by its own spring pressure resisting force from the compaction of material from the open end until it is pushed from the concave side of the dome to re-position or remove it.

In addition to the various advantages described hereinabove, the exothermal vaporizer described herein addresses a number of drawbacks and dependencies of current electric devices or otherwise experienced by known vaporizer devices and provides a seemingly low-tech approach to accomplish the task of vaporizing fluids and other smoking materials without using an electric element or any of its associated circuits or components. Moreover, the exothermal vaporizer accomplishes one or more of the foregoing tasks through the use of an innovative design and precise, yet durable non-electronic heat transfer and thermal feedback components.

The exothermal vaporizer described herein is designed to function reliably when heated with almost any heat source of sufficient thermal intensity. Moreover, the described vaporizer will function similarly on a warm calm day, as well as a brutally cold windy one. In the middle of the woods without any electricity, it can still be reliably and consistently activated with a lighter, or even a burning stick out of the campfire.

In addition, through the use of the non-electric temperature indicator, this device allows and creates a new level of independence from the traditional approach to vaporizers. By separating the heat source and control from the vaporizing device, many advantages become apparent. The most significant ones being the miniaturization and weight reduction in comparison to the above described heat source integrated devices. One example of the contrast of the exothermal vaporizer to the current integrated devices is the ability to easily hold the device in the user's mouth between the lips in a similar fashion to a cigarette. Without the weight of the battery, and the associated control componentry commonly found in electronic devices this becomes reasonable again. The user may now hold the device in their mouth while using it, and still have both hands free to attend to a task.

Likewise, one or more examples of a counter flow design exothermal vaporizer and a modular exothermal vaporizer are provided which have various additional advantages, such as: the condenser tube may be titanium or another suitable material; the condenser may thread into the mouthpiece and be adjustable to modulate and/or regulate the flow ratio of dilution air and produced vapor; the tip and the mouthpiece may integrate into the body with friction fit O-rings—which allows for tool-less assembly and disassembly as well as thermal isolation; and the O-rings may thermally and mechanically isolate the tip from the body allowing the use of thermally conductive materials for construction without the concern of excessive thermal conduction and/or uncomfortable surface temperatures affecting the user. Moreover, this design provides for a wide range of material choices for the different components (such as the titanium tip, wood, glass, metal or ceramic body) as long as the point of interface between the components is standardized and consistent. Additionally, the inverse induction airflow path for means of regulating and adjusting air/vapor concentration also serves several additional and important functions, for example, but not limited to: the flow path creates a counter flow heat exchanger whereby the incoming air in the process of cooling the air/vapor output through the wall of the condenser tube, scavenges the heat and the incoming air is thereby pre-warmed which reduces the temperature differential between the dilution and/or displacement air and the vaporization temperature of the desired compound(s) therefore maintaining vaporization temperature in the extraction chamber for either a longer period of time or permitting a larger mass of air and vapor to be heated/produced before falling below the minimum temperature threshold; the coaxial arrangement allows for a substantial reduction in size over other methods of cooling and/or tempering vapor output from vaporizers; and permitting an adjustable chamber size and easily removable and replaceable screens and other accessories for vaporization of fluids and resins— which may be retained using internal and/or external retaining rings and/or O-rings, either with a corresponding groove or without.

A new ability is also provided to a vaporizer, namely the ability to use new material(s) in specific areas of the unit where their respective characteristics would be most beneficial such as a metal extraction tip which includes the chamber and diffuser disc. For example, creating this component from a metal or otherwise thermally conductive material facilitates a more even distribution of heat from the heat source to the target material. In comparison, previous attempts to use thermally conductive materials resulted in the entire device becoming uncomfortably hot quickly limiting its usefulness. Uniquely, the exothermal vaporizer devices having the various components described herein permit heating of the material contained within the device to be smoked or inhaled such that the temperature exceeds the ignition temperature of the material without promoting combustion of the material. This permits extended time at operational temperature, and allows a slow decrease in temperature across the operational range thereby maximizing extraction. Among other reasons noted above, this advantage is accomplished at least in part because there is no airflow within the vaporizer until the user draws on it.

In addition to the foregoing, the design of the body with a dilution air induction, diffuser disc, and modulation system including a condenser tube for the collection of resins and extracts produced during use means this device also functions in a smoking application substantially better than most dedicated smoking apparatus. To further elaborate, current smoking devices are typically rudimentary in nature and the added features of this design of device can improve the smoking experience by providing the user additional means of adjusting the strength of the smoked extract as well as providing a more simple manner of separating and retaining some of the less desirable heavy tars an resins in a simple to remove and/or clean condenser tube.

Further, the condenser tube addresses one of the more significant operational issues of traditional smoking devices without such an element. The issue referred to is the undesirable accumulation of resinous deposits. These deposits are typically a combination of ash as well as distilled tars and resins with additional hydrocarbons and other incomplete combustion byproducts. As these deposits are accumulated in traditional devices they begin to obstruct the air and smoke flow path eventually rendering the device either unusable of difficult to use. The condenser tube by its design both in placement in the body with the inverse induction airflow and its corresponding smoke and dilution airflow acceleration, as well as the divergent shape following the induction of the dilution air and vapor/smoke mixture reduces the propensity of the high condensation constituents of the smoke or vapor to condense in the restricted portion of the condenser tube. In addition, as in the vaporizer use, the condenser tube functioning as a counter flow heat exchanger also helps cool the produced smoke as it traverses the condenser tube towards the mouthpiece or exit.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

It should be noted that references to relative positions (e.g., "top" and "bottom") in this description are merely used to identify various elements as are oriented in the Figures. It should be recognized that the orientation of particular components may vary greatly depending on the application in which they are used.

For the purpose of this disclosure, the term "coupled" means the joining of two members directly or indirectly to one another. Such joining may be stationary in nature or moveable in nature. Such joining may be achieved with the two members or the two members and any additional intermediate members being integrally formed as a single unitary body 104 with one another or with the two members or the two members and any additional intermediate members being attached to one another. Such joining may be permanent in nature or may be removable or releasable in nature.

It is also important to note that the construction and arrangement of the system, methods, and devices as shown in the various examples of embodiments is illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements show as multiple parts may be integrally formed, the operation of the interfaces may be reversed or otherwise varied, the length or width of the structures and/or members or connector or other elements of the system may be varied, the nature or number of adjustment positions provided between the elements may be varied (e.g. by variations in the number of engagement slots or size of the engagement slots or type of engagement). The order or sequence of any process or method steps may be varied or re-sequenced according to alternative embodiments. Other substitutions, modifications, changes and omissions may be made in the design, operating conditions and arrangement of the various examples of embodiments without departing from the spirit or scope of the present inventions.

While this invention has been described in conjunction with the examples of embodiments outlined above, various alternatives, modifications, variations, improvements and/or substantial equivalents, whether known or that are or may be presently foreseen, may become apparent to those having at least ordinary skill in the art. Accordingly, the examples of embodiments of the invention, as set forth above, are intended to be illustrative, not limiting. Various changes may be made without departing from the spirit or scope of the invention. Therefore, the invention is intended to embrace all known or earlier developed alternatives, modifications, variations, improvements and/or substantial equivalents.

The technical effects and technical problems in the specification are exemplary and are not limiting. It should be noted that the embodiments described in the specification may have other technical effects and can solve other technical problems.

The invention claimed is:

1. A modular exothermal vaporizer comprising:
a modular assembly of components, said components comprising:
a tip having a first end and a second end spaced from the first end of the tip, the tip having a hollow interior that extends between and is open on the first end and the second end of the tip, a portion of hollow interior of the tip comprising an extraction chamber and a diffuser removably retained in the hollow interior of the tip;
a body comprising a first end and a second end spaced from the first end, the body having a hollow interior that extends between and is open on the first end and the second end, the body being removably coupled with the tip on the first end of the body and a condenser comprising a hollow tubular member removably retained within the body extending an approximate length of the body and terminating adjacent the diffuser, an air gap surrounding the condenser between an exterior surface of the condenser and an interior surface of the body, extending the approximate length of the body, the body also having a mouthpiece on the second end of the body opposite the tip; and
a temperature indicating cap which is removable from the tip;
wherein the tip, the diffuser, the condenser, and the mouthpiece are removably and interchangeably assembled in the exothermal vaporizer by a friction fit assembly enabled by a plurality of O-rings positioned on the tip, the condenser, and/or the mouthpiece, the O-rings also being configured to provide an insulative interface between heated and unheated components of the assembled exothermal vaporizer.

2. The modular exothermal vaporizer of claim 1, wherein one or more grooves are provided on the tip, condenser, and/or mouthpiece, and O-rings are provided in the one or more grooves.

3. The modular exothermal vaporizer of claim 1, wherein the O-rings comprise an interface between exothermal vaporizer components composed of different material.

4. The modular exothermal vaporizer of claim 1, wherein the extraction chamber comprises a reservoir which is fillable with a smoking or vaping material.

5. The modular exothermal vaporizer of claim 4, wherein a wicking material is in communication with the reservoir.

6. The modular exothermal vaporizer of claim 1, comprising one or more apertures on the body.

7. The modular exothermal vaporizer of claim 1, wherein the condenser has a smaller cross-sectional area than the body and is removably retained in position in the body by the mouthpiece.

8. The modular exothermal vaporizer of claim 1, wherein the diffuser is a circumferential compression fit diffuser disc insertable into and removable from the exothermal vaporizer, and retained by a spring pressure resisting force in a groove.

9. The modular exothermal vaporizer of claim 1, wherein the tip, the diffuser, the mouthpiece, the body, the condenser, and the temperature indicating cap are provided in a kit.

10. An exothermal vaporizer comprising:
a modular assembly of components, said components comprising:
  a body comprising a first end and a second end spaced from the first end, the body having a hollow interior that extends between and is open on the first end and the second end;
  a tip having a first end and a second end spaced from the first end of the tip, the tip having a hollow interior that extends between and is open on the first end and the second end of the tip, the first end of the tip being removably coupled to the first end of the body, a portion of the hollow interior of the tip comprising an extraction chamber, the extraction chamber being positioned on the second end of the tip and a diffuser removably retained in the hollow interior of the tip;
  a condenser comprising a hollow tubular member removably retained within the body and extending an approximate length of the body and terminating adjacent the diffuser, and an air gap surrounding the condenser between an exterior surface of the condenser and an interior surface of the body, extending the approximate length of the body;
  the body also having a mouthpiece positioned on the second end of the body opposite the tip, the mouthpiece having an aperture extending therethrough; and
  a temperature indicating cap which is removable from the tip;
  wherein the tip, the diffuser, and the condenser are removably and interchangeably assembled in the exothermal vaporizer by a friction fit assembly having an insulative interface between heated and unheated components of an assembled exothermal vaporizer.

11. The exothermal vaporizer of claim 10, wherein the mouthpiece is integral with the body.

12. The exothermal vaporizer of claim 10, wherein one or more O-rings are positioned on either or both the tip and the condenser.

13. The exothermal vaporizer of claim 10, comprising one or more apertures on the body.

14. The exothermal vaporizer of claim 10, wherein the diffuser is a circumferential compression fit diffuser disc insertable into and removable from the exothermal vaporizer, and retained by a spring pressure resisting force in a groove.

15. The exothermal vaporizer of claim 10, wherein the tip, the diffuser, the body, the condenser, and the temperature indication cap are provided in a kit.

16. A modular exothermal vaporizer comprising:
a modular assembly of components, said components comprising:
  a tip having a first end and a second end spaced from the first end of the tip, the tip having a hollow interior that extends between and is open on the first end and the second end of the tip, a portion of hollow interior of the tip comprising an extraction chamber and a diffuser removably retained in the hollow interior of the tip;
  a body comprising a first end and a second end spaced from the first end, the body having a hollow interior that extends between and is open on the first end and the second end, the body being removably coupled with the tip on the first end of the body and a condenser removably retained within the body extending an approximate length of the body and terminating adjacent the diffuser, an air gap surrounding the condenser between an exterior surface of the condenser and an interior surface of the body, extending the approximate length of the body, the body also having a mouthpiece on the second end of the body opposite the tip; and
  a temperature indicating cap which is removable from the tip;
  wherein the tip, the diffuser, the condenser, and the mouthpiece are removably and interchangeably assembled in the exothermal vaporizer by a friction fit assembly enabled by a plurality of O-rings positioned on the tip, the condenser, and/or the mouthpiece, the O-rings also being configured to provide an insulative interface between heated and unheated components of the assembled exothermal vaporizer.

17. The modular exothermal vaporizer of claim 16, wherein the O-rings comprise an interface between exothermal vaporizer components composed of different material.

18. The modular exothermal vaporizer of claim 16, wherein the tip, the diffuser, the mouthpiece, the body, the condenser, and the temperature indicating cap are provided in a kit.

19. An exothermal vaporizer comprising:
a modular assembly of components, said components comprising:
  a body comprising a first end and a second end spaced from the first end, the body having a hollow interior that extends between and is open on the first end and the second end;
  a tip having a first end and a second end spaced from the first end of the tip, the tip having a hollow interior that extends between and is open on the first end and the second end of the tip, the first end of the tip being removably coupled to the first end of the body, a portion of the hollow interior of the tip comprising an extraction chamber, the extraction chamber being positioned on the second end of the tip and a diffuser removably retained in the hollow interior of the tip;

a condenser removably retained within the body and extending an approximate length of the body and terminating adjacent the diffuser, and an air gap surrounding the condenser between an exterior surface of the condenser and an interior surface of the body, extending the approximate length of the body;

the body also having a mouthpiece positioned on the second end of the body opposite the tip, the mouthpiece having an aperture extending therethrough; and a temperature indicating cap which is removable from the tip;

wherein the tip, the diffuser, and the condenser are removably and interchangeably assembled in the exothermal vaporizer by a friction fit assembly having an insulative interface between heated and unheated components of an assembled exothermal vaporizer.

20. The exothermal vaporizer of claim 19, wherein the mouthpiece is integral with the body.

21. The exothermal vaporizer of claim 19, wherein the tip, the diffuser, the body, the condenser, and the temperature indication cap are provided in a kit.

\* \* \* \* \*